US008334138B2

(12) United States Patent
Robins et al.

(10) Patent No.: US 8,334,138 B2
(45) Date of Patent: Dec. 18, 2012

(54) METHODS AND COMPOSITIONS FOR FEEDER-FREE PLURIPOTENT STEM CELL MEDIA CONTAINING HUMAN SERUM

(75) Inventors: Allan J Robins, Athens, GA (US); Thomas C Schulz, Athens, GA (US)

(73) Assignee: ViaCyte, Inc., San Diego, CA (US)

( * ) Notice: Subject to any disclaimer, the term of this patent is extended or adjusted under 35 U.S.C. 154(b) by 214 days.

(21) Appl. No.: 12/856,662

(22) Filed: Aug. 15, 2010

(65) Prior Publication Data
US 2010/0311164 A1 Dec. 9, 2010

Related U.S. Application Data

(63) Continuation of application No. 11/875,057, filed on Oct. 19, 2007.

(51) Int. Cl.
*C12N 5/00* (2006.01)
*C12N 5/02* (2006.01)
*C12N 5/10* (2006.01)
*C12N 5/071* (2010.01)

(52) U.S. Cl. ......... 435/408; 435/363; 435/366; 435/375

(58) Field of Classification Search ......................... None
See application file for complete search history.

(56) References Cited

U.S. PATENT DOCUMENTS

| 5,453,357 | A | 9/1995 | Hogan |
| 6,200,806 | B1 | 3/2001 | Thomson |
| 6,800,480 | B1 | 10/2004 | Bodnar et al. |
| 2003/0143736 | A1* | 7/2003 | Bongso et al. ............. 435/366 |
| 2005/0233446 | A1 | 10/2005 | Parsons et al. |
| 2006/0051862 | A1* | 3/2006 | Amit et al. ................. 435/366 |
| 2007/0122392 | A1 | 5/2007 | Gerecht-Nir et al. |
| 2009/0104696 | A1 | 4/2009 | Robins et al. |

FOREIGN PATENT DOCUMENTS

| WO | WO-9732033 | 9/1997 |
| WO | WO-9843679 | 10/1998 |
| WO | WO-9953021 | 10/1999 |
| WO | WO-0027995 | 5/2000 |

OTHER PUBLICATIONS

Stojkovic et al. "Human-Serum Matrix Supports Undifferentiated Growth of Human Embryonic Stem Cells", Stem Cells 23:895-902, 2005.
WIPO, PCT International Search Report for PCT/US2008/080516, Jan. 12, 2009, pp. 1-2.

* cited by examiner

*Primary Examiner* — Joanne Hama
(74) *Attorney, Agent, or Firm* — The Law Office of Jane K. Babin, Professional Corporation; Jane K. Babin (57) ABSTRACT

The present invention provides compositions and methods for the culture and maintenance of pluripotent stem cells. More particularly, the present invention provides for compositions and methods for culturing, maintaining, growing and stabilizing primate pluripotent stem cells in a feeder-free defined media further comprising human serum, or a soluble attachment component of the human serum, for promoting cell attachment.

19 Claims, 3 Drawing Sheets

METHODS AND COMPOSITIONS FOR FEEDER-FREE PLURIPOTENT STEM CELL MEDIA CONTAINING HUMAN SERUM

RELATED APPLICATIONS

This application is a continuation of U.S. patent application Ser. No. 11/875,057 filed Oct. 19, 2007, the entire disclosure of which is incorporated herein by reference.

ACKNOWLEDGMENT OF FEDERAL RESEARCH SUPPORT

This invention was made, at least in part, with funding from NCRR (5R24RR021313-05). Accordingly, the United States Government has certain rights in this invention.

BACKGROUND OF THE INVENTION

1. Field of the Invention

The present invention generally relates to compositions and methods for culturing pluripotent stem cells and/or cancer stem cells comprising a defined culture medium containing human serum.

2. Background of the Invention

Embryonic stem (ES) cells are a powerful model system for the investigation of mechanisms underlying pluripotent cell biology and differentiation within the early embryo, as well as providing opportunities for genetic manipulation of mammals and resultant commercial, medical and agricultural applications. Furthermore, appropriate proliferation and differentiation of ES cells can potentially be used to generate an unlimited source of cells suited to transplantation for treatment of diseases that result from cell damage or dysfunction. Other pluripotent cells and cell lines including early primitive ectoderm-like (EPL) cells as described in International Patent Application WO 99/53021, in vivo or in vitro derived ICM/epiblast, in vivo or in vitro derived primitive ectoderm, primordial germ cells (EG cells), teratocarcinoma cells (EC cells), and pluripotent cells derived by dedifferentiation or by nuclear transfer will share some or all of these properties and applications. International Patent Application WO 97/32033 and U.S. Pat. No. 5,453,357 describe pluripotent cells including cells from species other than rodents. Human ES cells have been described in International Patent Application WO 00/27995, and in U.S. Pat. No. 6,200,806, and human EG cells have been described in International Patent Application WO 98/43679.

Yet, to date, only several sub-optimal methods for isolating and growing stem cells from primates have been reported. For example, murine embryonic stem cells are maintained in an undifferentiated state using feeder-free cultures supplemented with leukemia inhibitory factor (LIF). On the other hand, human embryonic stem cells differentiate when the cells are cultured without a feeder cell layer or conditioned medium from a suitable feeder cell line, even in the presence of LIF. Systems which employ feeder cells (or conditioned media from feeder cell cultures) typically use cells from a different species than that of the stem cells being cultivated, e.g., mouse embryonic fibroblasts (MEF) form the feeder layer in most reported undifferentiated growth of human embryonic stem cells. Moreover, reports of feeder-free systems typically require the use of conditioned medium from MEF cultures, which does not cure the need for non-xenogeneic products/agents. Even systems that employ human feeder cells have the drawback of exposing the undifferentiated cells to undefined culture conditions, and therefore, many stem cell culture conditions are often not reproducible.

Additionally, for most cell therapies, treatment requires extremely large quantities of pluripotent stem cells. Based on the cell numbers required for islet transplantation using the Edmonton protocol the estimated quantity of differentiated cells required is on the order of $10^9$ to $10^{10}$ cells/patient. Further, depending on the hES-derived differentiated target cell, the quantity of undifferentiated hESCs could be orders of magnitude higher.

There is a need, therefore, to identify methods and compositions for the culture, stabilization and large-scale production of a uniform population of primate pluripotent stem cells for therapeutic purposes; and wherein the culture compositions are defined and/or produced to GMP standard.

The present invention described in detail below provides methods and compositions to culture undifferentiated hESCs using agents which have not been exposed or derived from non-humans, thus providing a safer culture media.

SUMMARY OF THE INVENTION

The invention provides compositions and methods for a defined media that supports the long-term cultivation of undifferentiated stem cells. The media is substantially feeder-free (i.e., feeder cells or feeder cell-conditioned medium is not required), and substantially free of any matrix coating.

Thus, in one aspect, the invention concerns defined media useful in culturing stem cells, including undifferentiated pluripotent stem cells. In solution, the media is substantially isotonic as compared to the stem cells being cultured. In a given culture, the particular medium comprises a base medium and an amount of various factors necessary to support substantially undifferentiated growth of embryonic stem cells. In preferred embodiments, the base medium comprises salts, essential amino acids, a carbon source that can be metabolized by primate stem cells, and human serum. All these ingredients are supplied in an amount that will support substantially undifferentiated growth of primate stem cells.

In one embodiment, the invention provides a feeder-free primate pluripotent stem cell tissue culture composition containing an undifferentiated human embryonic stem cell (hESC), a defined culture media comprising human serum (hS), wherein the human serum further comprises at least one soluble attachment component having at least 100 kDa molecular weight, and wherein the composition is essentially free of feeder cells.

In another embodiment, the invention provides a feeder-free primate pluripotent stem cell tissue culture composition containing an undifferentiated human embryonic stem cell (hESC), a defined culture media comprising human serum (hS) or a soluble attachment component thereof, wherein the human serum further comprises at least one soluble attachment component having at least 100 kDa molecular weight, and wherein the composition is essentially free of feeder cells.

In still another embodiment, the invention provides a method of culturing primate embryonic stem cells in a feeder-free defined media by culturing the primate embryonic stem cells in a culture medium which can support stem cells, the culture medium being substantially free of feeder cells and further containing about 0.5% to about 2% human serum, the culturing step being conducted for over one month with the embryonic stem cells proliferating in culture while maintaining the potential of the stem cells to differentiate into derivatives of endoderm, mesoderm, and ectoderm tissues, and while maintaining the karyotype of the embryonic stem cells.

These and other embodiments of the invention will be described in greater detail herein.

Each of the limitations of the invention can encompass various embodiments of the invention. It is therefore anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

The phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

DETAILED DESCRIPTION OF THE INVENTION

Use of human serum as a matrix for the growth of human embryonic stem cells (hESCs) under feeder-free conditions is described by Stojkovic et al. (Stem Cells Express (2005) *Stem Cells* 23:895-902, originally published online May 11, 2005). The method involves coating plates with human serum (hS) for 1 hour at room temperature, followed by removal of excess serum and drying of plates for 1 hour at room temperature. The human serum was derived from male cloned blood, tested and found negative for hepatitis B surface antigen, anti-hepatitis C virus, and anti-HIV/HIV-2 by FDA-approved tests. Replating of hESC should also use serum precoated plates. In some embodiments, the human serum was used together with hESC-dF-conditioned media. The conditioned medium was derived from cultures of fibroblast-tike cells, which were derived from spontaneously differentiated hESCs, as described by Stojkovic et al.

The present invention, described in more detail below, provides for compositions and methods for culturing, maintaining and growing a uniform and undifferentiated primate pluripotent stem cell, and in particular, hESCs, in a defined media and in the absence of a matrix, feeder layer or plate coating.

Definitions

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement), or any web based dictionary. It is to be understood that as used in the specification and in the claims, "a" or "an" can mean one or more, depending upon the context in which it is used. Thus, for example, reference to "a cell" can mean that at least one cell can be utilized.

As used herein, the term "contacting" (i.e., contacting a cell e.g., a differentiable cell, with a compound) is intended to include incubating the compound and the cell together in vitro (e.g., adding the compound to cells in culture). It is understood that the cells contacted with the defined medium can be further treated with a cell differentiation environment to stabilize the cells, or to differentiate the cells.

As used herein, the term "stabilize," when used in reference to the differentiation state of a cell or culture of cells, indicates that the cells will continue to proliferate over multiple passages in culture, and preferably indefinitely in culture, where most, if not all, of the cells in the culture are of the same differentiation state. in addition, when the stabilized cells divide, the division typically yields cells of the same cell type or yields cells of the same differentiation state. A stabilized cell or cell population in general, does not further differentiate or de-differentiate if the cell culture conditions are not altered and the cells continue to be passaged and are not overgrown.

In one embodiment, the cell that is stabilized is capable of proliferation in the stable state indefinitely, or for at least more than 2 passages. In a more specific embodiment, the cells are stable for more than 3 passages, 4 passages, 5 passages, 6 passages, 7 passages, 8, passages, 9 passages, more than 10 passages, more than 15 passages, more than 20 passages, more than 25 passages, or more than 30 passages. In one embodiment, the cell is stable for greater than approximately 1 month, 2 months, 3 months, 4 months, 5 months, 6 months, 7 months, 8 months, 9 months, 10 months, or 11 months of continuous passaging. In another embodiment, the cell is stable for greater than approximately 1 year of continuous passaging. In one embodiment, stem cells are maintained in culture in a pluripotent state by routine passage in the defined medium until it is desired that they be differentiated. As used herein, the term "proliferate" refers to an increase in the number cells in a cell culture.

Hence, as used herein, the term "growth environment" is an environment in which stem cells (e. g., primate embryonic stem cells) will proliferate in vitro. Features of the environment include the medium in which the cells are cultured, and a supporting structure (such as a substrate on a solid surface) if present.

A "defined" medium refers to a biochemically defined formulation comprised solely of the biochemically-defined constituents. A defined medium may include solely constituents having known chemical compositions. A defined medium may also include constituents that are derived from known sources. For example, a defined medium may also include factors and other compositions secreted from known tissues or cells; however, the defined medium will not include the conditioned medium from a culture of such cells. Thus, a "defined medium" may, if indicated, include particular compounds added to form the culture medium.

As used herein, the term "basal medium" refers to a solution of amino acids, vitamins, salts, and nutrients that is effective to support the growth of cells in culture, although normally these compounds will not support cell growth unless supplemented with additional compounds. The nutrients include a carbon source (e.g., a sugar such as glucose) that can be metabolized by the cells, as well as other compounds necessary for the cells' survival. These are compounds that the cells themselves cannot synthesize, due to the absence of one or more of the gene(s) that encode the protein(s) necessary to synthesize the compound (e.g., essential amino acids) or, with respect to compounds which the cells can synthesize, because of their particular developmental state the gene(s) encoding the necessary biosynthetic proteins are not being expressed as sufficient levels. A number of base media are known in the art of mammalian cell culture, such as Dulbecco's Modified Eagle Media (DMEM), Knockout-DMEM (KO-DMEM), and DMEM/F12, although any base medium that supports the growth of primate embryonic stem cells in a substantially undifferentiated state can be employed. A "basal medium" as described herein also refers to the basal medium described in PCT/US2007/062755, filed Jun. 13, 2007, which is herein incorporated in its entirety.

The basal medium may or may not contain "exogenous insulin or insulin substitutes", which refers to insulin or insulin substitutes that is/are not intentionally added to the compositions or methods of the present invention. Thus, in certain embodiments of the present invention, the methods and compositions are free of insulin or insulin substitutes that are intentionally supplied. The compositions or methods may, however, not necessarily be free of endogenous insulin. As used herein, "endogenous insulin" indicates that the cultured cells may be producing insulin of their own accord when cultured according to the methods of the present invention. Endogenous insulin also may be used to indicate residual impurities from the primary cell culture or impurities from the starting materials. In specific examples, the compositions and methods of the present contain less than 50, 45, 40, 35, 30, 25, 20, 15, 10, 9, 8, 7, 6, 5, 4, 3, 2, 1, 0.5, 0.25, 0.1 μg/ml, or substantially no amounts of insulin.

To be clear, the term "insulin" refers to the protein, or variant or fragment thereof that binds to the insulin receptor in normal physiological concentrations and can induce signaling through the insulin receptor. The term "insulin" encompasses a protein having the polypeptide sequence of native human insulin, or of other mammalian insulin, or of any homologs or variants to these sequences. Additionally, the term insulin encompasses polypeptide fragments that are capable of binding to the insulin receptor to induce signaling through the insulin receptor. The term "insulin substitute" refers to any zinc containing compound that may be used in place of insulin to give substantially similar results as insulin. Examples of insulin substitutes include, but are not limited to zinc chloride, zinc nitrate, zinc bromide, and zinc sulfate.

Also to be clear, insulin-like growth factors are not insulin substitutes or homologs of insulin, as contemplated in the present invention. Accordingly, in another specific embodiment, the compositions and methods of the present invention comprise the use of at least one insulin-like growth factor (IGF) or a variant or a functional fragment thereof. In another embodiment, the compositions and methods of the present invention are free of any exogenous insulin-like growth factors (IGFs). In specific embodiments, the compositions and methods of the present invention contain less than 200, 150, 100, 75, 50, 25, 20, 15, 10, 9, 8, 7, 6, 5, 4, 3, 2, or 1 ng/ml of IGF-1.

The defined media and/or basal media can include "nonessential amino acid(s)", which refers to an amino acid species that need not be added to a culture medium for a given cell type, typically because the cell synthesizes, or is capable of synthesizing, the particular amino acid species. While differing from species to species, non-essential amino acids are known to include L-alanine, L-asparagine, L-aspartic acid, L-glutamic acid, glycine, L-proline, and L-serine.

The defined media and/or basal media can also include various growth factors, hence the term "growth factor", which may or may not be included in the defined media described herein, refers to a substance that is effective to promote the growth of stem cells and which, unless added to the culture medium as a supplement, is not otherwise a component of the basal medium. Put another way, a growth factor is a molecule that is not secreted by cells being cultured (including any feeder cells, if present) or, if secreted by cells in the culture medium, is not secreted in an amount sufficient to achieve the result obtained by adding the growth factor exogenously. Growth factors include, but are not limited to, basic fibroblast growth factor (bFGF), acidic fibroblast growth factor (aFGF), epidermal growth factor (EGF), insulin-like growth factor-I (IGF-I), insulin-like growth factor-II (IGF-II), platelet-derived growth factor-AB (PDGF), and vascular endothelial cell growth factor (VEGF), activin-A, and bone morphogenic proteins (BMPs), cytokines, chemokines, morphogens, neutralizing antibodies, other proteins, and other molecules including but not limited to heregulin as described in PCT/US07/062755, which is herein incorporated by reference in its entirety. The defined media culture as described herein also contains substantially no insulin or lacks substantial amounts of insulin.

The culture conditions described herein are "isotonic", which term refers to a solution having essentially the same tonicity (i.e., effective osmotic pressure equivalent) as another solution with which it is compared. In the context of cell culture, an "isotonic" medium is one in which cells can be cultured without an appreciable net flow of water across the cell membranes.

Also, the culture conditions described herein are solutions having "low osmotic pressure" which refers to a solution having an osmotic pressure of less than about 300 milliosmols per kilogram ("mOsm/kg").

Although, a conditioned medium is not employed in the present invention, as used herein, the phrase "conditioned medium" refers to a growth medium that is further supplemented with soluble factors derived from cells cultured in the medium. Techniques for isolating conditioned medium from a cell culture are well known in the art. As will be appreciated, conditioned medium is preferably essentially cell-free. In this context, "essentially cell-free" refers to a conditioned medium that contains fewer than about 10%, preferably fewer than about 5%, 1%, 0.1%, 0.01%, 0.001%, and 0.0001% than the number of cells per unit volume, as compared to the culture from which it was separated. However, it is contemplated that the skilled artisan can "substantially remove" one or more detectable components of a conditioned medium. For example, the skilled artisan can remove an amount of the detectable, known component(s) from the conditioned medium which results in a fractionated conditioned medium as compared to an unfractionated conditioned medium. Fractionation of a conditioned medium can be performed by any method (or combination of methods) suitable to remove the detectable component(s), for example, gel filtration chromatography, affinity chromatography, immune precipitation, size-exclusion devices etc.

"Human embryonic stem cells" or "hES cells" or "hESCs" or "stem cells" or "pluripotent stem cells" are cells obtained from an animal (e.g., a primate, such as a human) embryo. These terms and phrases are equivalent to the phrase, "differentiable cell". A "differentiable cell" is used to describe a cell or population of cells that can differentiate into at least partially mature cells, or that can participate in the differentiation of cells, e.g., fuse with other cells, that can differentiate into at least partially mature cells. As used herein, "partially mature cells" are cells that exhibit at least one characteristic of the phenotype, such as morphology or protein expression, of a mature cell from the same organ or tissue.

Differentiable cells, as used herein, may be pluripotent, multipotent, oligopotent or even unipotent, as defined in detail below. In certain embodiments of the present invention, the differentiable cells are pluripotent differentiable cells. In more specific embodiments, the pluripotent differentiable cells are selected from the group consisting of embryonic stem cells, ICM/epiblast cells, primitive ectoderm cells, primordial germ cells, and teratocarcinoma cells. In one particular embodiment, the differentiable cells are mammalian embryonic stem cells. In a more particular embodiment, the differentiable cells are human embryonic stem cells.

The invention also contemplates differentiable cells from any source within an animal, provided the cells are differentiable as defined herein. For example, differentiable cells may be harvested from embryos, or any primordial germ layer therein, from placental or chorion tissue, or from more mature tissue such as adult stem cells including, but not limited to adipose, bone marrow, nervous tissue, mammary tissue, liver tissue, pancreas, epithelial, respiratory, gonadal and muscle tissue. In specific embodiments, the differentiable cells are embryonic stem cells. In other specific embodiments, the differentiable cells are adult stem cells. In still other specific embodiments, the stem cells are placental- or chorionic-derived stem cells.

Of course, the invention contemplates using differentiable cells from any animal capable of generating differentiable cells, e.g., pancreatic type cells such as beta cells. The animals from which the differentiable cells are harvested may be vertebrate or invertebrate, mammalian or non-mammalian, human or non-human. Examples of animal sources include, but are not limited to, primates, rodents, canines, felines, equines, bovines and porcines.

The differentiable cells of the present invention can be derived using any method known to those of skill in the art. For example, human pluripotent cells can be produced using dc-differentiation and nuclear transfer methods. Additionally, the human ICM/epiblast cell or the primitive ectoderm cell used in the present invention can be derived in vivo or in vitro. Primitive ectodermal cells may be generated in adherent culture or as cell aggregates in suspension culture, as described in WO 99/53021. Furthermore, the human pluripotent cells can be passaged using any method known to those of skill in the art, including, manual passaging methods, and bulk passaging methods such enzymatic or non-enzymatic passaging.

As used herein, the term "differentiate" refers to the production of a cell type that is more differentiated than the cell type from which it is derived. The term therefore encompasses cell types that are partially and terminally differentiated.

In certain embodiments of the present invention, the term "enriched" refers to a cell culture that contains at least 50%, 55%, 60%, 65%, 70%, 75%, 80%, 85%, 90%, 95%, or 100% of the desired cell lineage.

As used herein, the term "substantially undifferentiated" cell culture refers to a population of stem cells containing at least about 50%, preferably at least. about 60%, 70%, or 80%, and even more preferably, at least about 90%, undifferentiated, stem cells. Fluorescence-activated cell sorting using labeled antibodies or reporter genes/proteins (e.g., enhanced green fluorescence protein [EGFP]) to one or more markers indicative of a desired undifferentiated state can be used to determine how many cells of a given stem cell population are undifferentiated. For purposes of making this assessment, one or more cell surface markers correlated with an undifferentiated state (e.g., SSEA-4, Tra-1-60, and Tra-1-81), as well as the typical pluripotent stem cell transcription factor marker, Oct-4, can be detected. Telomerase reverse transcriptase (TERT) activity and alkaline phosphatase can also be assayed. In the context of primate stem cells, positive and/or negative selection can be used to detect, for example, by immuno-staining or employing a reporter gene (e.g., EGFP), the expression (or lack thereof) of certain markers (e.g., Oct-4, SSEA-4, Tra-1-60, Tra-1-81, SSEA-1, SSEA-3, nestin, telomerase, Myc, p300, and Tip60 histone acetyltransferases, and alkaline phosphatase activity) or the presence of certain post-translational modifications (e.g., acetylated histones), thereby facilitating assessment of the state of self-renewal or differentiation of the cells. Also, undifferentiated cells described herein have typical stem cell morphology which is well described in the art.

"Pluripotent" refers to cells that are capable of differentiating into one of a plurality of different cell types, although not necessarily all cell types. An exemplary class of pluripotent cells is embryonic stem cells, which are capable of differentiating into any cell type in the human body. Thus, it will be recognized that while pluripotent cells can differentiate into multipotent cells and other more differentiated cell types, the process of reverse differentiation (i.e., de-differentiation) is likely more complicated and requires "re-programming" the cell to become more primitive, meaning that, after re-programming, it has the capacity to differentiate into more or different cell types than was possible prior to re-programming.

"Totipotent" refers to cells that are capable of differentiating into any cell type, including pluripotent, multipotent, and fully differentiated cells (i.e., cells no longer capable of differentiation into various cell types), such as, without limitation, embryonic stem cells, neural stem cells, bone marrow stem cells, hematopoietic stem cells, cardiomyocytes, neuron, astrocytes, muscle cells, and connective tissue cells.

As used herein, "multipotent cells" include cells and their progeny, which may be able to differentiate into, or give rise to, multipotent, oligopotent and unipotent progenitor cells, and/or one or more mature or partially mature cell types, except that the mature or partially mature cell types derived from multipotent cells are limited to cells of a particular tissue, organ or organ system. For example, a multipotent hematopoietic progenitor cell and/or its progeny possess the ability to differentiate into or give rise to one or more types of oligopotent cells, such as myeloid progenitor cells and lymphoid progenitor cells, and also give rise to other mature cellular components normally found in the blood. "Oligopotent cells" include cells and their progeny whose ability to differentiate into mature or partially mature cells is more restricted than multipotent cells. Oligopotent cells may, however, still possess the ability to differentiate into oligopotent and unipotent cells, and/or one or more mature or partially mature cell types of a given tissue, organ or organ system. One example of an oligopotent cell is a myeloid progenitor cell, which can ultimately give rise to mature or partially mature erythrocytes, platelets, basophils, eosinophils, neutrophils and monocytes. "Unipotent cells" include cells and their progeny that possess the ability to differentiate or give rise to other unipotent cells and/or one type of mature or partially mature cell type.

Also, a "normal" stem cell refers to a stem cell (or its progeny) that does not exhibit an aberrant phenotype or have an aberrant genotype, and thus can give rise to the full range of cells that can be derived from such a stem cell. In the context of a totipotent stem cell, for example, the cell could give rise to, for example, an entire, normal animal that is healthy. In contrast, an "abnormal" stem cell refers to a stem cell that is not normal, due, for example, to one or more mutations or genetic modifications or pathogens. Thus, abnormal stem cells differ from normal stem cells.

Again, although the present invention does not employ a tissue culture vessel coating or matrix, e.g., an "extracellular matrix", an "extracellular matrix" or "matrix" as used herein, refers to one or more substances that provide substantially the same conditions for supporting cell growth as provided by an extracellular matrix synthesized by feeder cells. The matrix may be provided on a substrate (e.g., fibronectin, collagen, MATRIGEL™, and the like).

As used herein, the term "feeder cells" or "feeder cell layers" are cells which grow in vitro and are co-cultured with a target cell, e.g., co-cultured with stem cells. As used herein, the term "essentially free of a feeder cell" or "feeder-free" and equivalents thereof, refer to tissue culture conditions that do not contain intentionally added feeder cells. Also, a cell culture is "essentially feeder-free" when it does not contain exogenously added conditioned medium taken from a culture of feeder cells nor exogenously added feeder cells in the culture, where "no exogenously added feeder cells" means that cells to develop a feeder cell layer have not been purposely introduced for that reason. Of course, if the cells to be cultured are derived from a seed culture that contained feeder cells, the incidental co-isolation and subsequent introduction into another culture of some small proportion of those feeder cells along with the desired cells (e. g., undifferentiated primate stem cells) should not be deemed as an intentional introduction of feeder cells. In such an instance, the culture contains a de minimus number of feeder cells. By "de minimus", it is meant that number of feeder cells that are carried over to the instant culture conditions from previous culture conditions where the differentiable cells may have been cultured on feeder cells. Similarly, feeder cells or feeder-like cells that develop from stem cells seeded into the culture shall not be deemed to have been purposely introduced into the culture.

The present invention contains a defined media further containing various amounts of human serum, for example, from about 0.5% to about 40%, from about 0.5% to about 30%, from about 0.5% to about 20%, from about 0.5% to about 10%, from about 0.5% to about 5%, from about 0.5% to about 3%, from about 0.5% to about 2%, and from about 0.5% to about 1%. However, typical defined media stem cell cultures use the term "essentially serum-free" which refers to exogenously added serum. Serum added in such media is typically in greater amounts than that described herein. Of course, if the cells being cultured produce some or all of the components of serum, or if the cells to be cultured are derived from a seed culture grown in a medium that contained serum, the incidental co-isolation and subsequent introduction into another culture of some small amount of serum (e.g., less than about 1%) should not be deemed as an intentional introduction of scrum.

As used herein, the term "size-exclusion device" refers to filtration devices capable of separating materials on the basis of their size. One non-limiting exemplary class of such devices is the filtration-type class, wherein sample components are separated on the basis of molecular weight through a matrix that allows small molecules to pass through more rapidly than larger molecules. Typically, filtration-type devices are characterized by a molecular weight cutoff that represents an upper limit of the molecular weight of molecules that are able to pass through the matrix. Typically, a sample solution or reaction mixture is forced through the molecular weight separation matrix by application of centrifugal force (by centrifugation) or positive pressure (e.g., application of gaseous pressure or application of a piston above the solution or reaction mixture). In some embodiments, the matrix is provided as a membrane. Such devices typically have an integral filter material between an upper and a lower chamber. Examples of such size-exclusion devices are the commercially available Microcon 300, 100, 50, 30, 3, and Centricon 3K, 30K, 50K, 100K, and 300K (all from Millipore), and Nanosep available in 10K, 30K, 100K and 300k cutoffs (all from Pall Corp.). The Microcon and Centricon units are the same devices, but differ in volume of solution that can be used. Also available is a 96-well plate, for processing many samples simultaneously. Use of such a multi-sample well plate renders the purification process less burdensome. Thus, in some embodiments, the "size-exclusion device" comprises a porous, size-discriminating barrier that allows smaller molecules (e.g., smaller than a predetermined molecular weight cutoff, as exemplified above) to pass through while retaining larger molecules (which have molecular weights greater than the cutoff). For example, such a device can be an ultrafiltration device, comprising a porous membrane, such as a Microcon or Centricon filtration device of the type just described. The molecular weight cut-off of the size exclusion device is selected to retain desired components, and allow undesired species to pass through. Thus, such embodiments operate by retaining larger molecules which can be transiently trapped in pores of the particles while smaller molecules pass through with bulk eluant, such that smaller molecules elute first. In some embodiments, the size-exclusion device has a 300K cut off, or a 100K cut off, or a 30K cut off. It will be appreciated, however, that size exclusion device having any suitable cut-off can be employed in the present methods.

The methods described herein comprise plating the cells in an adherent culture. As used herein, the terms "plated" and "plating" refer to any process that allows a cell to be grown in adherent culture. As used herein, the term "adherent culture" refers to a cell culture system whereby cells are cultured on a solid surface, which may in turn be coated with an insoluble substrate that may in turn be coated with another surface coat of a substrate, such as those listed below, or any other chemical or biological material that allows the cells to proliferate or be stabilized in culture. The cells may or may not tightly adhere to the solid surface or to the substrate. The substrate for the adherent culture may comprise any one or combination of MATRIGEL™ polyornithine, laminin, poly-lysine, purified collagen, gelatin, fibronectin, tenascin, vitronectin, entactin, heparin sulfate proteoglycans, poly glycolytic acid (PGA), poly lactic acid (PLA), and poly lactic-glycolic acid (PLGA). Furthermore, the substrate for the adherent culture may comprise the matrix laid down by a feeder layer, or laid down by the pluripotent human cell or cell culture.

As used herein, the phrase "soluble attachment component" or "soluble attachment agent" or equivalents thereof, refers to a soluble component, e.g., a polypeptide, contained in human serum which functions to promote pluripotent stem cell attachment to a substrate, e.g., to promote pluripotent stem cells to attach to plastic tissue culture vessel. The soluble attachment component is at least 100 kDa, at least 150 kDa, at least 200 kDa, at least 250 kDa, or at least 300 kDa or higher, and remains in suspension or is a solute in solution. That is, such a soluble attachment component is not provided for coating of tissue culture vessel and therefore does not form the basis of a matrix coating as typically understood in primate stem cell cultures.

As used herein, the term, "tissue culture vessel" or "tissue culture plastic" or equivalents thereof refers to any and all containers, now known or later discovered, commonly used to culture and grow stem cells. For example, some tissue culture vessels have a base with a bottom wall and a plurality of sidewalls extending up from said bottom wall, a cover extending across said sidewalls and opposed to the bottom wall. Alternatively, the cover can be formed with at least one opening and a septum extending across said opening for permitting access to interior portions of said vessel by another device. Still, many tissue culture vessels are of generally prismatic shape (e.g., bioreactors) with a plurality of upstanding sidewalls extending between opposed top and bottom walls. The sidewalls generally are constructed so that the length and width of the vessel exceed the height. As a result, the bottom wall of the vessel defines a fairly large surface area relative to the volume of the vessel. A tubular neck typically is formed at one of the sidewalls of the vessel to provide access to the interior. The outer surface of the neck may be formed with an array of threads for receiving a cap. Thus, one skilled in the art will recognize that the present invention and use of media containing hS to promote cell attachment to the base, bottom or sidewalls of a tissue culture or tissue culture-like vessel, encompasses many and potentially all tissue culture vessels independent of shape, size and volume.

The present invention may also be understood more readily by reference to the following detailed description of the preferred embodiments of the invention and the Examples included herein. However, before the present compositions and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art.

Defined Culture for Growth, Proliferation and Maintenance of Pluripotent Stem Cells The present invention describes use of methods and compositions for a defined media, which was first described in PCT/US2007/062755, filed Jun. 13, 2007, which is herein incorporated in its entirety.

In guiding hESC technology toward the clinic, one key issue to be addressed is a lack of standardization in the culture and maintenance of hESCs. In the absence of mouse embryonic fibroblast (MEF) feeder layers, many researchers rely on "conditioning" in which medium is first exposed to MEFs to acquire soluble factors that support the propagation of undifferentiated hESCs in culture. It has been difficult to discern how MEF conditioning enables hESCs to maintain an undifferentiated state. Other common features of more recently developed hESC culture conditions include the presence of FGF2, the absence of serum, and the presence of a serum substitute such as KnockOut Serum Replacer (KSR-Invitrogen, proprietary formulation). Other factors suggested to play a role in supporting the maintenance of hESCs include TGFβ1, activin A (ActA), PDGF and sphingosine-1-phosphate, BIO, a small molecule inhibitor of GSK3β, and neurotrophins. Several defined medium systems have been described for hESCs and are based upon FGF2 in combination with nodal, TGFβ1, GABA, pipecolic acid, plus lithium chloride, Wnt3a plus April/BAFF, or the N2/B27 supplements. While these studies have focused on identifying growth factors and conditions that support the proliferation of undifferentiated hESCs, little is known about the cell surface receptors that are activated when hESCs are exposed to conditions favorable for self-renewal.

The methods and compositions of a defined media which supports hESC self-renewal is described in PCT/US2007/062755 and incorporated herein by reference in its entirety. A benefit of using a defined media is that the ingredients comprising the media are known and have known quantities. In contrast, an undefined medium has some complex ingredients, consisting of a mixture of many, many chemical species in unknown proportions. The reasons for utilizing chemically defined media are also pragmatic because such media is reproducible at different times and in different laboratories. Defined media can be varied in a controlled manner and, are free of unknown biological activities, such as enzymes and, alternatively, growth factors, which may affect the responses being studied.

The compositions and methods of the present invention are useful for culturing cells, in particular, differentiable cells. It is understood that at different points during culturing the differentiable cells, various components may be added to the cell culture such that the medium can contain components other than those described herein.

The compositions and methods comprise a basal salt nutrient solution. As used herein, and as described in PCT/US2007/062755, which is herein incorporated in its entirety, a basal salt nutrient solution refers to a mixture of salts that provide cells with water and certain bulk inorganic ions essential for normal cell metabolism, maintain intra- and extra-cellular osmotic balance, provide a carbohydrate as an energy source, and provide a buffering system to maintain the medium within the physiological pH range. Examples of basal salt nutrient solutions include, but are not limited to, Dulbecco's Modified Eagle's Medium (DMEM), Minimal Essential Medium (MEM), Basal Medium Eagle (BME), RPMI 1640, Hams F-10, Ham's F-12, β-Minimal Essential Medium (βMEM), Glasgow's Minimal Essential Medium (G-MEM), and Iscove's Modified Dulbecco's Medium, and mixtures thereof. In one particular embodiment, the basal salt nutrient solution is an approximately 50:50 mixture of DMEM and Ham's F12.

In one embodiment, the compositions and methods of the present invention provide for a soluble attachment factor or agent, such soluble attachment components is contained in the human serum, which at the appropriate concentration range facilitates hESC cell attachment to tissue culture type plastic. Such cell attachment allows cells to attach and form a monolayer but in the absence of a feeder layer or a substrate coating, e.g., a matrix coating, MATRIGEL™ and the like. Preferably, human serum is utilized in order to provide an animal-free environment. Human serum can be obtained from any commercial supplier of tissue culture products, examples include Gibco-Invitrogen Corporation (Grand Island, N.Y. USA), Sigma (St. Louis Mo., USA) and the ATCC (Manassas, Va. USA). The serum used in the present invention is provided at a concentration range of about 0.1% to about 20%, more preferably about 0.1 to about 3%, more preferably about 0.5 to about 2%, more preferably about 0.5 to about 1.5%, and more preferably about 0.5 to about 1%.

In another aspect of the invention, the human serum is fractionated using microfluidic size-exclusion devices. Various microfluidic devices for filtration are commercially available. The devices can be used, for example, for gel filtration, size-exclusion filtration, ion-exchange filtration, or combinations of these filtration techniques. For example, filtration materials can be loaded and/or included in the devices, and can include small beads of filtration materials. Size-exclusion materials can be used that can retain smaller molecules of an aqueous sample while allowing larger molecules of the sample to pass through or around. For example, P-10BIO- GEL materials from Bio-Rad can be used and are composed of acrylamide particles that are have 45-100 μm in average particle size diameter. Samples can be manipulated through the microfluidic devices via gravity pressure differentials, or centripetal force, for example. The resulting filtrates that elute from the devices can then be analyzed, used, or subsequently passed on through the device to a subsequent stage of processing. In one aspect of the invention, the size-exclusion device has a 300 KDa cut off, or a 100 KDa cut off, or a 30 KDa cut off spin columns, e.g., Microcon spin columns.

According to other aspects of the invention, the filter fit material can be "press fit" into the respective chamber, placed in the respective chamber, or otherwise positioned in the respective chamber.

In another aspect of the invention, the gel filtration material can be disposed in a channel of the microfluidic device. The gel filtration material can be loaded into the device by pipetting into an input opening of the device and/or drawing the material into the device by using vacuum force, for example, applied to an output opening of the device. A channel of the device can be filled with a gel filtration material by pressure loading the gel filtration material through an input opening of the device to dispense the gel filtration material in a channel or chamber of the device. Once the channel is filled with hydrated gel filtration material, the device can be centrifuged to de-water the gel filtration material and to "pack" the gel filtration material, forming a purification column. This process can be used to prepare the device for sample filtration and can be used to remove unnecessary or excess water or buffer from the gel filtration material.

Thus, it will be appreciated that microfluidic size exclusion devices, in general, having any suitable filtration material and/or agent and having any suitable molecular weight cut-off can be employed in the present methods; and the compositions and methods described herein are not limited to the described devices.

Compositions and methods of the invention can also include at least one activator of an FGF receptor, including any of the FGF polypeptides, functional fragments thereof or variants thereof. Compositions and methods of the invention can include serum albumin (SA), e.g., bovine SA (BSA) or human SA (HAS), at least one insoluble substrate. For example, the differentiable cells may be placed on a cell culture surface that comprises compounds as, but not limited to, polystyrene and polypropylene.

The present invention is distinguished from other defined culture conditions in that the compositions and methods comprise proliferating pluripotent stem cells substantially free of feeder cells or layers, or "feeder-free", or a conditioned medium produced by collecting medium from a culture of feeder cells. In addition, the compositions and methods of the present invention do not require for the pluripotent stem cells to proliferate and grow on any substrate, including any substrate coated with extracellular matrix components (i.e., collagen, laminin, fibronectin, proteoglycan, entactin, heparan sulfate, and the like, alone or in various combinations), or MATRIGEL™. The concentration of human serum provided herein is sufficient to promote cell attachment and promote growth and proliferation of undifferentiated pluripotent stem cells.

In one embodiment, differentiable cells are contacted with at least one of the compositions of the invention in the absence a feeder cell layer, such that the cells are maintained in an undifferentiated state for at least one (1) to twelve (12) months or more. Pluripotency can be determined through characterization of the cells with respect to surface markers, transcriptional markers, karyotype, and ability to differentiate to cells of the three germ layers. These characteristics are well known to those of ordinary skill in the art.

It is contemplated that the differentiable cells can be passaged using enzymatic, non-enzymatic, or manual dissociation methods prior to and/or after contact with the defined medium of the invention. Non-limiting examples of enzymatic dissociation methods include the use of proteases such as trypsin, collagenase, dispase, and ACCUTASE™. In one embodiment, ACCUTASE™ is used to passage the contacted cells, When enzymatic passaging methods are used, the resultant culture can comprise a mixture of singlets, doublets, triplets, and dumps of cells that vary in size depending on the enzyme used. A non-limiting example of a non-enzymatic dissociation method is a cell dispersal buffer. Manual passaging techniques have been well described in the art, such as in Schulz et al., 2004 Stem Cells, 22(7):1218-38. The choice of passaging method is influenced by other culture conditions, including but not limited to feeders and/or extracellular matrices; although neither is anticipated in the present invention.

The disaggregation solution used in the methods of the present invention can be any disaggregation solution capable of breaking apart or disaggregating the cells into single cells, without causing extensive toxicity to the cells. Examples of disaggregation solutions include, but are not limited to, trypsin, ACCUTASE™, 0.25% Trypsin/EDTA, TrypLE, or VERSENE™ (EDTA) and trypsin. The methods of the present invention need not result in every cell of the confluent layer being disaggregated into single cells, provided that at least a few single cells are disaggregated and capable of being re-cultured.

The compositions and methods of the invention may contain virtually any combination of the components set out above or described elsewhere herein, e.g. PCT/US2007/062755. As one skilled in the art would recognize, the components of the compositions and methods of the invention will vary according to the protocol design. Accordingly, one embodiment of the present invention relates to culturing differentiable cells in 96-well plates and/or 384-well plates, or in larger vessels including, bioreactors, cell factories, or other automated, or GMP compliant, specialized devices available or devised by one skilled in the art. Thus, the methods of the present invention are not limited to specific culture chamber dimensions.

The culture methods of the invention comprise culturing stem cells such as primate embryonic stem cells in a growth environment that is essentially feeder-free and which comprises a defined, isotonic culture medium according to the invention and in the absence of a matrix. Such defined, isotonic culture media contain the essential components that are required for maintaining the stem cells (e.g., pluripotent stem cells) in a substantially undifferentiated state (or their functional equivalents). The cells can be cultured in such an environment in any suitable culture vessel under conditions that allow an undifferentiated state to be maintained.

Using such methods, populations of stem cells, including substantially undifferentiated primate stem cells, e.g., human embryonic stem cells, can be isolated from the resulting cell cultures, thereby representing another aspect of the invention. Such populations can be isolated by any suitable technique. Such techniques include affinity chromatography, panning, and fluorescence-assisted cell sorting. Such techniques each employ one or more separation reagents (for example, but not restricted to, antibodies and antibody fragments, reporter genes/proteins, etc.) that are specific for a cell-based marker indicative of an undifferentiated state. In the context of substantially undifferentiated human embryonic stem cells, such markers include, for example, but are not restricted to the transcriptional factor Oct4, and cell surface markers SSEA-4, Tra-1-60, and Tra-1-81. Other markers include telomerase, Myc, p300, and Tip60 histone acetyltransferases, acetylated histones, and alkaline phosphatase and typical stem cell morphology.

Method for Identifying Factors/Agents Capable of Promoting Pluripotent Stem Cell Growth and/or Differentiation Another embodiment of the invention relates to a method of using stem cells to identify factors that promote the cells' differentiation, or, alternatively, the cells' continued maintenance and stabilization in a substantially undifferentiated state. Briefly, in the context of differentiation or maintenance of a substantially undifferentiated state, such methods involve, for example, exposing a test compound to substantially undifferentiated primate embryonic stem cells that are being cultured in a defined, isotonic culture medium of the invention. Following exposure to the test compound, the cells are assessed to determine if they have been better maintained in a substantially undifferentiated state or induced to differentiate. If the cells have been better maintained in a substantially undifferentiated state, the test compound can be identified as one that promotes an undifferentiated state or self-renewal of primate pluripotent stem cells. If the cells have been induced to differentiate, the test compound can be identified as one that promotes differentiation of substantially undifferentiated primate pluripotent stem cells. The differentiating cells may be followed to determine their developmental fate, in other words, to determine what cell lineage they become as a result of differentiating. In the context of de-differentiation, cells of a more differentiated state are exposed to one or more compounds and then assessed to determine if the exposure resulted in cells of a more primitive type (e.g., a pluripotent stem cell) than those initially exposed to the test compound. If so, the compound that produces the effect is identified as one that promotes de-differentiation, or reprogramming, of cells. Preferably, these and other screening methods according to the invention are conducted in a high throughput manner, such that numerous compounds can be simultaneously screened.

The cell types that differentiate from differentiable cells have several uses in various fields of research and development including but not limited to drug discovery, drug development and testing, toxicology, production of cells for therapeutic purposes as well as basic science research. These cell types express molecules that are of interest in a wide range of research fields. These include the molecules known to be required for the functioning of the various cell types as described in standard reference texts. These molecules include, but are not limited to, cytokines, growth factors, cytokine receptors, extracellular matrix, transcription factors, secreted polypeptides and other molecules, and growth factor receptors.

It is to be understood that one of the benefits provided by culturing stem cells by methods described in the present invention is the reduction and avoidance of contamination of the stem cells with pathogens or antigens foreign to the stem cells. This type of contamination can occur when feeder cells from a different species or from a different and unrelated individual of the same species are used. The methods of the invention are intended to avoid as much as possible further testing of the stem cell lines (including testing for pathogen content). In some embodiments, it is anticipated that the human stem cells and/or their differentiated progeny can be transplanted into a genetically related individual without prior testing for some or all pathogen content.

The cell lines may be tested prior to or after cryopreservation for their genotype and histocompatibility haplotype, as appropriate. Genotype testing refers to determining the genotype of the stem cell lines at one or more resolution levels. It is not necessary to determine the genotype of the cell line at single nucleotide resolution. Rather, the genotyping must only be carried out at a resolution level that allows one of ordinary skill to determine the similarity between the stem cell line and any intended recipient thereof. Genotyping can be carried out in a number of ways including but not limited to restriction fragment length polymorphism (RFLP), single nucleotide polymorphisms (SNPs) and the like.

The cell lines and/or their progeny can also be tested for their histocompatibility haplotype; or to determine if they are "normal" or "abnormal" stem cells. A histocompatibility haplotype is a set of alleles at the histocompatibility gene loci that is used by the immune system to distinguish between self and non-self (i.e., foreign) tissues and/or cells. In humans, the major histocompatibility (MHC) locus is composed of four loci on the short arm of chromosome 6. Humans also have a set of minor histocompatibility loci. As an example, human leukocyte antigen (HLA) typing is commonly performed for various transplants such as hematopoietic cell transplants. Major and minor histocompatibility antigens are present on cell surfaces and are recognized by the immune system as an indicator of the origin of the cell or tissue. Cells or tissues that are viewed as foreign will usually be rejected by the recipient via a host versus graft immune response. However, it is sometimes possible to overcome some differences in histocompatibility, particularly those in the minor histocompatibility loci, using for example immunosuppressive drugs such as but not limited to cyclosporin A, FK506, rapamycin, cyclophosphamide (CY), procarbazine (PCB), and antithymocyte globulin (ATG). Additionally, certain tissues are less susceptible to differences at for example the HLA loci in humans. These tissues include but are not limited to liver, kidney, and the central nervous system. It has recently been reported that embryonic stem cells possess immune privileged properties (Li et al. Stem Cells 2004 33:448-456).

Kits

The present invention also relates to kits, wherein the kit comprises a basal salt nutrient solution and at least one compound capable of stimulating ErbB2-directed tyrosine kinase activity. In one embodiment, the kits comprise at least one ErbB3 ligand, as described herein. In another embodiment, the kits comprise more than one ErbB3 ligand. In another embodiment, the kits comprise at least one of TGF-β or a TGF-β family member or a variant or functional fragment thereof as described herein. In yet another embodiment, the kits comprise more than one of TGF-β or a TGF-β family member or a variant or functional fragment thereof. In still another embodiment, the kits comprise at least one fibroblast growth factor or variant or functional fragment thereof. In another embodiment, the kits comprise more than one fibroblast growth factor or variant or functional fragment thereof. In a specific embodiment, the kits comprise at least one of FGF-7, FGF-l0, FGF-22 or variants or functional fragments thereof. In another embodiment, the kits comprise serum albumin. In still another embodiment, the kits comprise serum and/or at least one insoluble substrate as described herein and/or at least one disaggregation solution.

The kits of the invention may contain virtually any combination of the components set out above or described elsewhere herein, which includes but is not limited to the described defined media culture comprising human serum or a high molecular weight fraction thereof. As one skilled in the art would recognize, the components supplied with kits of the invention will vary with the intended use for the kits. Thus, kits may be designed to perform various functions set out in this application and the components of such kits will vary accordingly.

Throughout this application, various publications are referenced. The disclosures of all of these publications and those references cited within those publications in their entireties are hereby incorporated by reference into this application in their entirety in order to more fully describe the state of the art to which this invention pertains.

EXAMPLES

Example 1

Proliferation of Undifferentiated Pluripotent Stem Cells in a Feeder-Free Culture Containing Small Quantities of Human Serum To elucidate a media and cell culture condition that is compatible with the expected regulatory guidelines governing clinical safety and efficacy, Applicants have provided a hESC scale-up strategy which facilitates this requirement as described in more detail below. Long-term cultivation of undifferentiated hESCs in a feeder-free, conditioned-medium-free, and matrix-free medium is crucial for providing an unlimited supply of cells for cell-based therapies, as well as for directing the lineage-specific differentiation of hESCs.

Previously, the minimal essential conditions needed to support the long-term growth of undifferentiated hESCs were determined. See PCT/US2007/062755). The developmental stage of the stem cells was assessed, in part, based on morphological analysis, as well as by expression of cell surface markers and alkaline phosphatase analysis.

In order to establish a xeno-free, feeder-free, conditioned-medium-free, and matrix-free growth culture environment, a culture system incorporating the defined media described herein and in PCT/US2007/062755 was used. In addition, to maintain culture conditions which are free of non-human animal products, but which facilitated cell binding or attaching to or laying down on the plastic and growth, human serum was used. The NIH-registered BG01, BG02 and BG03 hESC lines, as well as CyT49, a hESC line isolated using human feeder cells under GMP conditions (Novocell, San Diego, Calif.) were cultured in the defined media including about 0.5 to 2% human serum (hS) for about 12 to 24 hours at 37° C. Most commercially available lots of human serum can be used, for example, ALBUMARC human serum was employed for certain hESC cultures described herein. ALBUMARC is a registered name for human serum from the American Red Cross Blood Services. It is noteworthy, that the undifferentiated hESCs were grown and maintained in a non-coated tissue culture vessel. The amount of hS utilized promotes cell attachment to tissue culture plastic such that coating of the tissue culture vessel, for example, with ECM, fibronectin, collagen and/or MATRIGEL™ and the like is not required. Also increased concentrations of hS can be employed, for example up to 20% of hS has been used to culture and maintain hESC cultures.

The elimination of a matrix requirement provides for a more efficient culture and growth of the cells. Cell cultures were routinely passaged with ACCUTASE. After seeding in the tissue culture plate for about 12-24 hours, the hESCs appeared morphologically normal. Also, karyotype analyses of hESCs grown in the defined media and hS were performed using standard G-banding techniques.

To determine if the hS was heat sensitive or heat labile, and whether it effected hESC growth, the hS was first heated to about 50-60° C. for about 20-60 minutes and then added to the defined media at a concentration of about 0.5 to 2%. hESCs in this medium did not proliferate significantly, and most died after about 1-3 days post-seeding. Hence, a cell attachment promoting component of the hS is heat sensitive and at about 50-60° C., activity decreased significantly and hESCs did not survive. The hESCs likely did not survive due to the heat sensitivity of one or more soluble attachment factors in the hS, which can become heat-inactivated. Heat-inactivation of these soluble attachment factor(s) prevents pluripotent stem cell attachment to the plastic, which attachment promotes growth and maintenance of the hESCs.

To further determine the approximate size of these soluble attachment factors, it was postulated that specific fractions in the hS were responsible for potentiating growth and proliferation of the hESCs. To determine which fractions, the hS was fractionated using various size-exclusion devices, e.g., Microcon 300K, 100K and 30K cut-off spin columns. The use of these cut-off spin columns allows certain molecular weight proteins to pass through and be collected as the eluant or retentate fraction. hESCs were then cultured in the defined media, containing one of various retentate fractions substantially as described above. Retentate fractions from the 300K and 100K cut-off spin columns appeared to contain particular soluble attachment factors and/or agents which promoted undifferentiated hESC growth and proliferation. Undifferentiated hESC growth and proliferation was consistent with various retentate fractions from the 300K and 100K cut-off spin columns, and was independent of the commercial source of the (non-heat treated) hS. Thus, those soluble attachment factors capable of being retained in the retentate fraction in 300K to 100K cut-off spin columns, were important and capable of promoting growth and proliferation.

Figure 1:
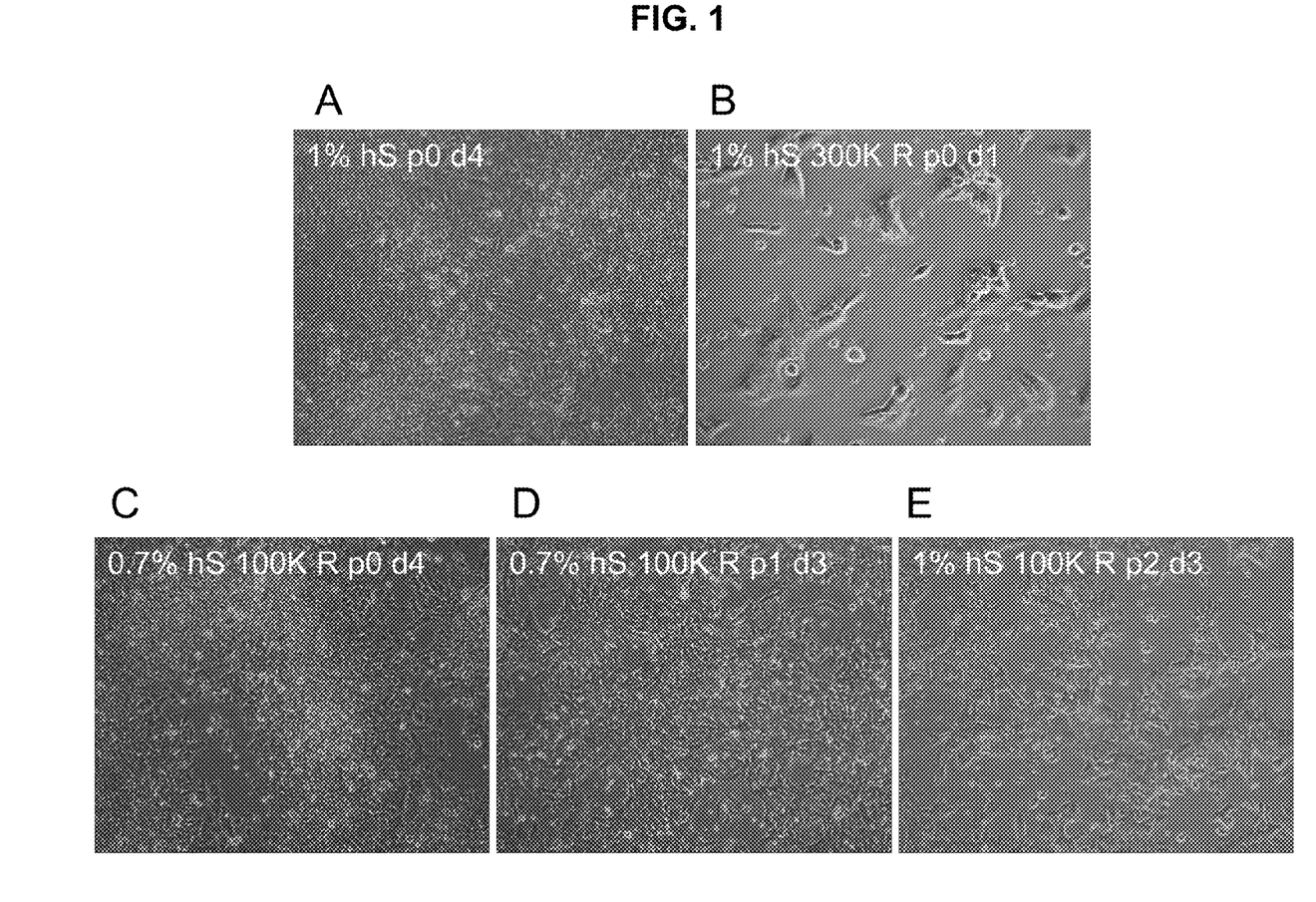
FIGS. 1A-1E show photomicrograph images of pluripotent stem cell cultures in a defined media containing various concentrations of human serum at passages 0 to 3 (p0 to p3) and days 1 through 4 (d1-d4).

FIGS. 1A-E are images of hESCs (BG02 cells) growing in defined media (DC-HAIF) on uncoated tissue culture vessels with different amounts of human serum. FIG. 1A is an image of hESCs after 4 days of growth in DC-HAIF containing 1% whole serum on uncoated tissue culture vessels. The cells were incubated with DC-HAIF plus 1% hS for about 24 hours and then the media was replaced with DC-HAIF. FIG. 1B is a hESC image after 1 day of growth in DC-HAIF containing 1% of hS which was partially fractionated (retentate fraction was used) on a 300K cut-off spin column. FIG. 1C is an hESC image after 4 days of growth in DC-HAIF containing about 0.7% hS which was partially fractionated (retentate fraction was used) on a 100K cut-off spin column. FIG. 1D is a hESC image after 1 passage and after 3 days of growth in DC-HAIF media containing about 0.7% hS which was partially fractionated (retentate fraction) on a 100K cut-off spin column. FIG. 1E is a hESC image of a serially passaged (2 passages) population cultured in DC-HAIF and about 1% hS which was partially fractionated (retentate fraction) on a 100K cut-off spin column.

Additionally, to determine whether stem cell morphology was effected upon serial passaging of the hESCs under these culture conditions, the undifferentiated hESCs were serially passaged for about 2, 3, 4, 5, 6, 7, 8, 9, and 10 times and the like. Undifferentiated hESCs split to single cells can also grow and proliferate substantially as described. With an aid of a microscope, all cultures appeared morphologically normal. In contrast, when the undifferentiated hESCs were serially passaged using whole hS, there was some deterioration in the morphological quality of the hESC cultures as compared to hESCs passaged using retentate fractions as described above. However, to restore typical hESC cellular morphology, the hS can be partially purified by filtering about 20% hS using a 100K cut-off spin column, the collected eluant/retentate fraction then diluted back to the original volume. Thus, fractionating the hS as described herein largely avoided deterioration in morphological quality of hESC cultures with serial passaging. This was also observed with hS concentrations between about 0.5 to 1.5%.

To demonstrate the self-renewal of undifferentiated hESCs maintained under the above-described defined biologics-free culture conditions, hESCs were enzymatically treated, dissociated into a single cell suspension, and then cultivated under the defined conditions substantially as described above. Undifferentiated mature-sized single-cell-derived hESC colonies began to appear after about 4, 5, 6, and 7 days in vitro.

The plating efficiency was comparable to that observed in hESCs cultured in DC-HAIF as described in PCT/US2007/062755 or cultured in DC-HAIF media using MATRIGEL™ as an ECM. The plating efficiency using MATRIGEL™ was significantly higher than using MEF-CM or feeders. One explanation is that the dissociated single cells seeded efficiently in hS containing DC-HAIF or defined hESC media as compared to other feeder and or feeder and matrix type cultures.

This example identifies the minimal essential components necessary to maintain primate embryonic stem cells, in particular hESCs, in a healthy, undifferentiated state capable of both prolonged propagation and then directed differentiation. Having discerned these molecular requirements, it became possible to derive conditions that would permit the substitution of poorly-characterized and unspecified biological additives and substrates (including those derived from animals) with entirely defined constituents. This defined culture system has the advantage of allowing hESCs to be expanded efficiently and stably following enzyme-mediated dissociation. Therefore, this study provides a viable approach for providing a large supply of well-characterized, clinically-acceptable, healthy cells for cell-based therapies. In addition, having established individual components required for the undifferentiated growth of hESCs, it is now possible to assess more accurately the effects of other growth factors and compounds on the developmental fate of hESCs. As will be appreciated, defined media are crucial for directing a requisite number of pluripotent hESCs efficiently, uniformly, stably, and reproducibly towards a specific lineage for therapeutic purposes. Also, FISH analyses of BG02 cells maintained for 10 passages in DC-HAIF with 1% 100K human serum fraction exhibited normal counts for human Chromosome 12 (hChr 12; 98% two copy, n=591) and hChr 17 (98% two copy, n=578). Hence, self-renewal of pluripotent hESCs in media containing a small percentage of human serum does not select for the aneuploidies typically observed in hESCs.

Example 2

Long Term-Self Renewal of HESCS using 100K Human Serum Fraction

Figure 2:
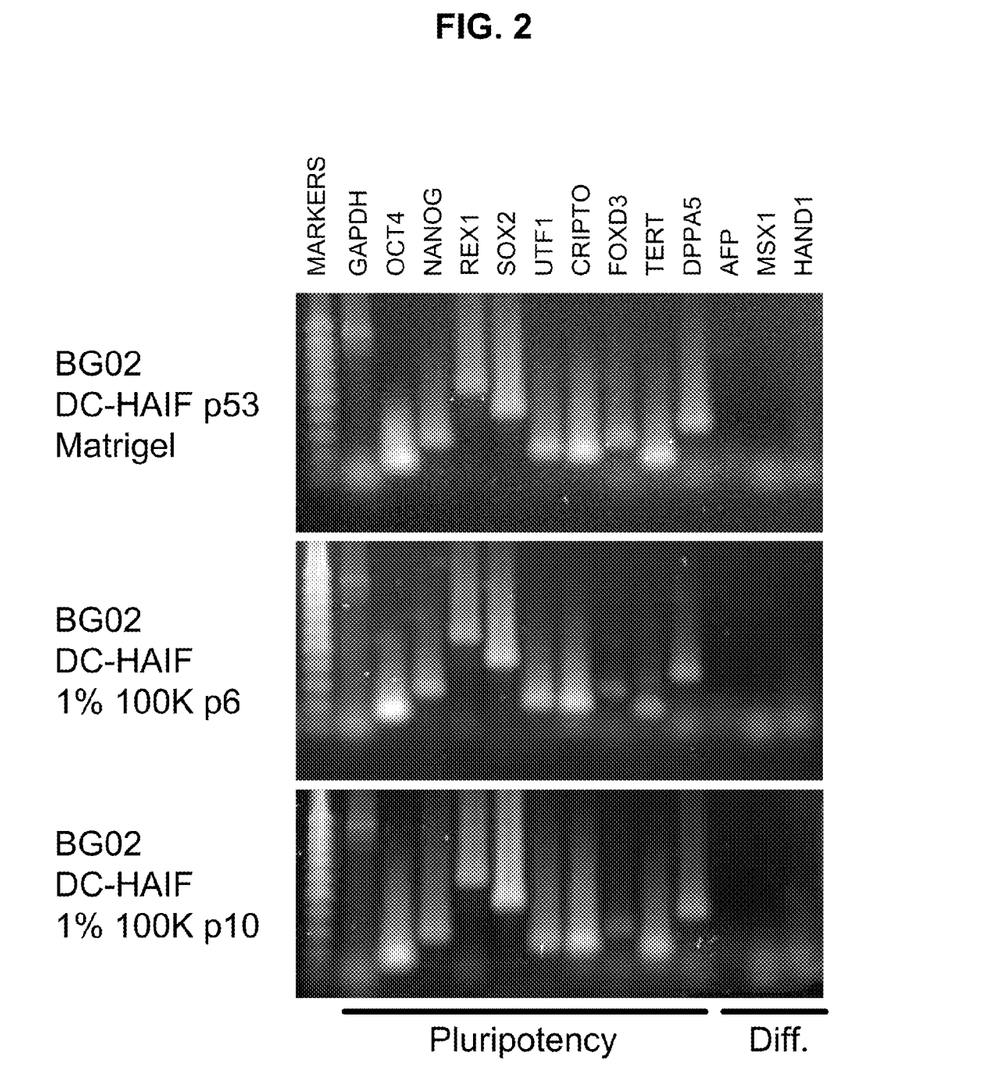
FIG. 2 is a photomicrograph of an agarose gel containing RT-PCR results using OCT4, NANOG, REX1, SOX2, UTF1, CRIPTO, FOXD3, TERT, DPPA5 AFP, MSX1 and HAND1 cell markers of pluripotent hESCs (lanes 2-11, left to right) and differentiated hES-derived cells (lanes 12-14).

To be useful, any hESC culture medium has to be able to support long-term or prolonged self-renewal of the cells, i.e. for several passages. To demonstrate that the DC-HAIF containing hS media described herein can support long-term or prolonged self-renewal of hESCs, hESCs were cultured in DC-HAIF with about 1% 100 k human serum retentate fraction. To make certain that the hESCs maintained their pluripotency and did not spontaneously differentiate to different cell lineages, RT-PCR analysis was performed using cell markers well known in the art for describing and identifying pluripotent stem cells and/or differentiated stem cell-derived lineages. RT-PCR was performed on hESC cultures after 6 and 10 passages. In control cultures, RT-PCR was performed after 53 passages in defined media alone (FIG. 2). FIG. 2 shows that typical pluripotent stem cell markers were expressed in cultures from 6 (middle panel), 10 (bottom panel) and 53 (top panel) passages, for example, expression of OCT4, NANOG, REX1, SOX2, UTFI, CRIPTO, FOXD3, TERT and DPPA5. In contrast, markers typical of differentiated stem cell-derived lineages, for example, α-fetoprotein (AFP), MSXI, HANDI were not detected in these cultures. Thus, these data indicate that hESCs grown in the DC-HAIF with human serum media promote long term or prolonged self-renewal of pluripotent hESCs and not spontaneous differentiation into hES-derived cell lineages.

Example 3

HESCS Maintained in a Defined Media Containing 100K Human Serum Fraction can Differentiate into Various Cell Lineages To determine whether hESCs cultured as described herein could also differentiate to various hES-derived cell lineages, BG02 cells were differentiated to hES-derived cells in vitro (FIG. 3). hESCs were first maintained for 3 splits for 5 to 7 days in 0.7% or 1% hS fractionated using a 100K cut-off spin column. hESCs were then induced to differentiate on days 5 and 7, respectively, to definitive endoderm by exposing cultures to RPMI containing 2% fatty acid-free BSA, 25 ng/ml Wnt3a, 100 ng/ml Activin A and 8 ng/ml FGF2 for 24 hours, followed by RPMI containing 2% BSA, 100 ng/ml Activin A and 8 ng/ml FGF2 for two more days (d3 of differentiation). Further differentiation of the definitive endoderm cells to foregut endoderm was performed by exposing the cells to RPMI containing 2% BSA, 50 ng/ml FGF7 and 0.25 μM KAAD-cyclopamine for about 2-3 more days (d6 of differentiation). The cell cultures were examined by qPCR as described previously in D'Amour et al 2005, Nat Biotechnol. 23:1534-1541 and D'Amour et al 2006, Nat Biotechnol. 24:1392-1401, which are herein incorporated by reference in their entirety.

Figure 3:
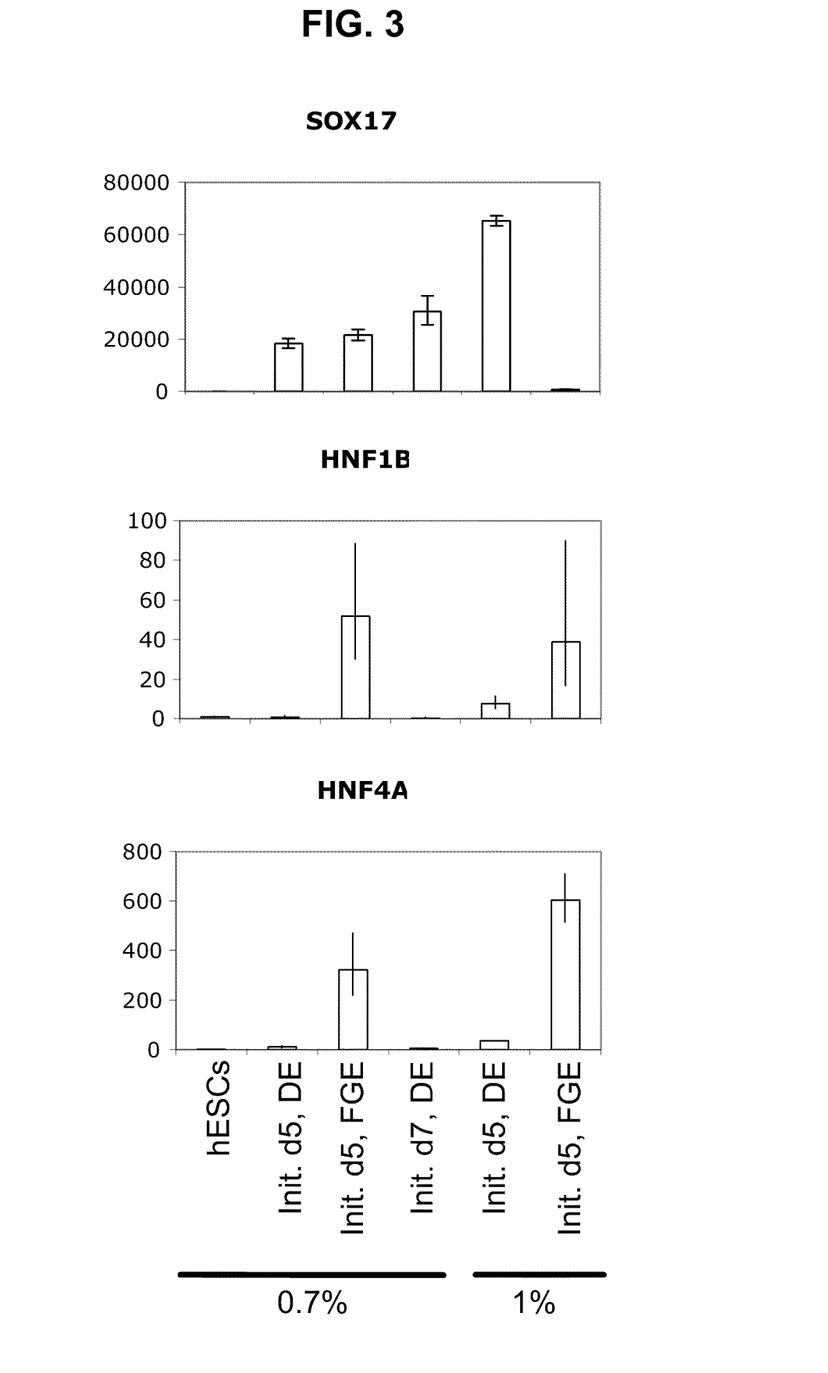
FIG. 3 is a graph describing normalized, relative expression of SOX17, HNF1B and HNF4A in pluripotent hESCs (passage 67; lane 1, left), d3 definitive endoderm cultures (lanes 2, 4 and 5), and d5 foregut endoderm cultures (lanes 3 and 6).

The hES-derived cells (definitive endoderm) were examined on the third day of differentiation. FIG. 3 shows graphs describing normalized expression levels of various cell markers at d3 (definitive endoderm, DE) and d5 (foregut endoderm, FG). The top panel of FIG. 3 shows that SOX17 expression is increased significantly at d3 (definitive endoderm); whereas expression levels of HNF1B and HNF4A were upregulated in d5 (foregut) samples. Expression levels of SOX17, HNF1B and HNF4A in definitive endoderm and foregut type hES-derived cells is consistent with that described in D'Amour et al. 2005 and 2006, supra.

These data demonstrate that the described feeder-free cultures maintained using retentate fractions from 100K human serum fraction can differentiate effectively to various hES-derived cell lineages including definitive endoderm and foregut endoderm.

All patents and patent applications, publications, scientific articles, and other referenced materials mentioned in this specification are indicative of the levels of skill of those skilled in the art to which the invention pertains, and each of which is hereby incorporated by reference to the same extent as if each reference had been incorporated by reference in its entirety individually.

Applicants reserve the right to physically incorporate into this specification any and all materials and information from any such patents and patent applications, publications, scientific articles, electronically available information, and other referenced materials or documents.

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

As used in the claims below and throughout this disclosure, the phrase "consisting essentially of" is meant to include any elements listed after the phrase, and also may include other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

We claim:

1. A tissue culture composition consisting of:
   a. a primate pluripotent stem cell;
   b. a defined culture medium that supports proliferation of the primate pluripotent stem cell in an undifferentiated state; and
   c. sufficient human serum to promote attachment of the primate pluripotent stem cell to a tissue culture vessel, wherein the tissue culture vessel is uncoated and free of matrix,
   wherein the composition does not comprise conditioned media and is essentially free of feeder cells.

2. The composition of claim 1, wherein the primate pluripotent stem cell is a human pluripotent stem cell.

3. The composition of claim 2, wherein the human pluripotent stem cell is a human embryonic stem cell (hESC).

4. The composition of claim 1, comprising human serum at a concentration of about 0.1% to about 20% of the medium.

5. The composition of claim 4, wherein the concentration of human serum in the medium is between about 0.5% and about 20%; between about 0.5% and about 10%; between about 0.5% and about 5%; between about 0.5% and about 3%; between about 0.5% and about 2%; or between about 0.5% and about 1%.

6. The composition of claim 5, wherein the concentration of human serum in the medium is selected from the group consisting of about 0.5%, about 0.7%, about 1%, about 1.5%, about 2%, about 3%, about 5%, about 10%, and about 20%.

7. The composition of claim 1, wherein the defined culture medium is free of non-human animal proteins.

8. A method of culturing a primate pluripotent stem cell comprising:
   a. plating the primate pluripotent stem cell in a unconditioned and feeder-free combination consisting of:
      i. a defined culture media medium that supports proliferation of the primate pluripotent stem cell in a undifferentiated state; and
      ii. sufficient human serum to promote attachment of the primate pluripotent stem cell to a tissue culture vessel, wherein the tissue culture vessel is uncoated and is free of matrix,
   b. incubating the primate pluripotent stem cell plated in step a, thereby culturing the primate pluripotent stem cell.

9. The method of claim 8, wherein the primate pluripotent stem cell is a human pluripotent stem cell.

10. The method of claim 8, wherein the human pluripotent stem cell is a human embryonic stem cell (hESC).

11. The method of claim 8, wherein the combination comprises human serum at a concentration of about 0.1% to about 20% of the medium.

12. The method of claim 11, wherein the concentration of human serum in the combination is between about 0.5% and about 20%; between about 0.5% and about 10%; between about 0.5% and about 5%; between about 0.5% and about 3%; between about 0.5% and about 2%; or between about 0.5% and about 1%.

13. The method of claim 12, wherein the concentration of human serum in the combination is selected from the group consisting of about 0.5%, about 0.7%, about 1%, about 1.5%, about 2%, about 3%, about 5%, about 10%, and about 20%.

14. The method of claim 8, wherein the primate pluripotent stem cell is cultured for over one month and continues to proliferate in an undifferentiated state.

15. The method of claim 14, wherein the undifferentiated state of the primate pluripotent stem cell is determined by observing at least one characteristic selected from the group consisting of: primate pluripotent stem cell morphology; normal karyotype; ability to differentiate into derivatives of endoderm, mesoderm, and ectoderm; and expression of at least one pluripotent stem cell marker.

16. The method of claim 15, wherein the marker is selected from Oct4, SSEA-4, Tra-1-81, and Tra-1-60.

17. The method of claim 8, wherein the primate pluripotent stem cell continues to proliferate without differentiation for 2, 3, 4, 5, 6, 7, 8, 9, or 10 serial passages.

18. The method of claim 17, wherein the primate pluripotent stem cell is passaged by enzymatic dissociation and replating.

19. The method of claim 18, wherein the enzymatic dissociation generates a single cell suspension.

* * * * *